United States Patent
Weyl et al.

(10) Patent No.: US 7,210,331 B2
(45) Date of Patent: May 1, 2007

(54) DETECTING ELEMENT FOR DETERMINING THE CONCENTRATION OF A GAS COMPONENT IN A MEASURING GAS, AND METHOD FOR MANUFACTURING THE DETECTING ELEMENT

(75) Inventors: Helmut Weyl, Wiesbaden (DE); Bernhard Wild, Markgroeningen (DE); Rainer Maier, Tamm (DE); Michael Liebler, Leonberg (DE); Peter Dettling, Waiblingen (DE); Lars Berger, Moeglingen (DE)

(73) Assignee: Robert Bosch GmbH, Stuttgart (DE)

( * ) Notice: Subject to any disclaimer, the term of this patent is extended or adjusted under 35 U.S.C. 154(b) by 61 days.

(21) Appl. No.: 10/871,221

(22) Filed: Jun. 17, 2004

(65) Prior Publication Data

US 2005/0072211 A1    Apr. 7, 2005

(30) Foreign Application Priority Data

Jun. 17, 2003    (DE) .................................. 103 27 186

(51) Int. Cl.
*G01N 27/00*    (2006.01)

(52) U.S. Cl. ................ 73/23.31; 73/23.32; 204/242; 204/428

(58) Field of Classification Search ............... 73/23.31, 73/23.32; 204/242, 428
See application file for complete search history.

(56) References Cited

U.S. PATENT DOCUMENTS

| | | | |
|---|---|---|---|
| 5,785,829 A * | 7/1998 | Watanabe | 204/427 |
| 5,800,689 A | 9/1998 | Hori et al. | |
| 5,874,663 A * | 2/1999 | Fukaya et al. | 73/23.32 |
| 5,874,664 A * | 2/1999 | Watanabe et al. | 73/23.32 |
| 6,222,372 B1 * | 4/2001 | Fukaya et al. | 324/464 |
| 6,303,013 B1 * | 10/2001 | Watanabe et al. | 204/428 |
| 6,319,378 B1 * | 11/2001 | Kojima et al. | 204/427 |
| 6,340,809 B2 * | 1/2002 | Yamada | 219/543 |
| 6,360,581 B1 * | 3/2002 | Murase et al. | 73/23.2 |
| 6,415,647 B1 * | 7/2002 | Yamada et al. | 73/31.05 |
| 6,463,788 B2 * | 10/2002 | Nakano et al. | 73/31.05 |
| 6,484,561 B2 * | 11/2002 | Jackson et al. | 73/31.05 |

(Continued)

FOREIGN PATENT DOCUMENTS

DE        196 11 572        9/1997

(Continued)

*Primary Examiner*—Michael Cygan
(74) *Attorney, Agent, or Firm*—Kenyon & Kenyon LLP

(57) ABSTRACT

A detecting element is described, in particular a gas sensor for detecting the concentration of a gas component in a measuring gas, including a sensor element which is exposable to the measuring gas and has a connecting end section which is contacted by connecting cables and is exposed to a reference gas atmosphere. The end section is accommodated in a protective sleeve having a radial opening over which a gas-permeable diaphragm covering the at least one radial opening is provided, the diaphragm, in turn, being engaged by a clamping sleeve having at least one radial opening. To avoid the axial penetration of liquids between the clamping sleeve and the diaphragm, which would cause the detecting element to malfunction, the clamping sleeve is caulked axially above and below the radial openings. Both caulking zones are designed in such a way that the diaphragm is compressed with increasing force from the inner caulking edges facing each other to the outer caulking edges facing away from each other.

5 Claims, 2 Drawing Sheets

U.S. PATENT DOCUMENTS 6,585,872 B2 * 7/2003 Donelon et al. ............ 204/424
6,726,819 B2 * 4/2004 Atsumi et al. .............. 204/428
2002/0144538 A1 10/2002 Yamada et al.

FOREIGN PATENT DOCUMENTS

| DE | 198 35 345 | 2/2000 |
| DE | 101 51 291 | 5/2002 |
| EP | 0899562 | 3/2003 |

* cited by examiner

DETECTING ELEMENT FOR DETERMINING THE CONCENTRATION OF A GAS COMPONENT IN A MEASURING GAS, AND METHOD FOR MANUFACTURING THE DETECTING ELEMENT

FIELD OF THE INVENTION

The present invention relates to a detecting element, in particular, a gas sensor for determining the concentration of a gas component in a measuring gas.

BACKGROUND INFORMATION

A known detecting element or gas sensor of, shown in German Published Patent Application No. 101 51 291 at FIG. 2, has a housing accommodating the sensor element, the connecting end section of the housing supporting the connecting end section of the sensor element having contact surfaces. The sensor element also includes a reference gas channel whose connecting end section ends in the interior of the connecting end housing section. The sensor element contact surfaces are electrically connected to contact parts which establish electrical connections to connecting cables via crimp joints. The connecting cables are routed from the housing through a gas-tight cable bushing that terminates the housing opening. A pot-shaped supporting element made of a high-temperature-resistant plastic, whose external surface is tapered in the direction of the pot opening, is provided in the contact area of the housing section. The inside sleeve has a plurality of radial openings in the tapered area. A gas-permeable hose which covers the radial openings is provided over the inside sleeve. Multiple radial openings, which are preferably aligned with the radial openings in the inside sleeve, are also provided in the housing so that a reference gas, e.g., ambient air, surrounding the outside of the housing can pass through the porous hose and enter the interior of the connecting-end housing section along the tapered supporting element via the radial openings in the inside sleeve. These design characteristics enable the reference gas to flow freely, thus preventing the gas sensor measurement results from being corrupted as a result of an excessively low or excessively high concentration of the reference gas and simultaneously preventing gushing water from penetrating the housing, which would cause the gas sensor to fail.

Another known detecting element, in particular for determining the oxygen concentration in the exhaust gas of internal combustion engines is shown in German Published Patent Application No. 198 35 345 and has a sensor element which is axially located in a metal housing and is contacted on its connecting end section by at least one connecting cable which is axially routed from the housing through a bush element. The connecting cable has insulation that includes a gas-permeable area, permitting the reference atmosphere surrounding the housing to enter the interior of the cable insulation, from where it reaches the housing interior. The gas-permeable area of the cable insulation, which is immediately adjacent to the cable-output end of the bush element, is surrounded by a porous hose made of a gas-permeable PTFE material so that a radial clearance remains between the porous PTFE hose and the gas-permeable section of the cable insulation. An internal clamping sleeve, which has at least one radial hole in its section immediately adjacent to the bush element, is provided over the cable insulation above the bush element, maintaining a radial clearance. This internal clamping sleeve is inserted into one end of the hose made of PTFE material, while the other end of the hose is located between the bush element and an external clamping sleeve surrounding the bush element. The external clamping sleeve also has multiple radial holes. All structural components are interconnected in a gas-tight manner by applying caulking around the external clamping sleeve twice, leaving an axial clearance: once above the radial holes and once below them.

SUMMARY OF THE INVENTION

The detecting element according to the present invention has the advantage that, due to variable compression of the gas-permeable diaphragm—which is preferably designed as a porous PTFE hose—it prevents leaks in the caulking-around area in the outer and inner areas of each calking zone due to diaphragm destruction or damage caused by poor manufacturing conditions and/or high thermal loads.

While the external area of the diaphragm wall thickness is compressible, for example to approximately 10–20% of its original thickness, thereby reliably clamping the diaphragm, the caulking in the internal area merely reduces the diaphragm wall thickness to only 30–40%, for example, of its original thickness, which achieves a very efficient axial seal against vehicle-specific media such as water. A good seal in the internal area of the caulking zone also prevents any leakage paths from forming within the caulking zone in cases in which the diaphragm is damaged or even, in part, completely punctured in the external caulking areas due to the substantial reduction in wall thickness caused by poor manufacturing conditions or high thermal stress.

According to an advantageous embodiment of the present invention, the different degrees of compression of the diaphragm are achieved by designing the caulking in such a way that the radial distance between the clamping sleeve and the protective sleeve is reduced in the deformation areas produced by caulking in the clamping sleeve, starting from the inner caulking or deformation edges facing each other and extending to the outer calking or deformation edges facing away from each other.

According to alternative embodiments of the present invention, the decrease in radial clearance is continuous or stepped, and the compression of the diaphragm from the outer edges to the inner edges of the caulking zones takes place continuously or to different degrees in defined axially adjacent deformation zones of the deformation areas, the compression being most pronounced in the outer deformation zones and the compression being the least pronounced in the inner deformation zones.

DETAILED DESCRIPTION

Figure 1:
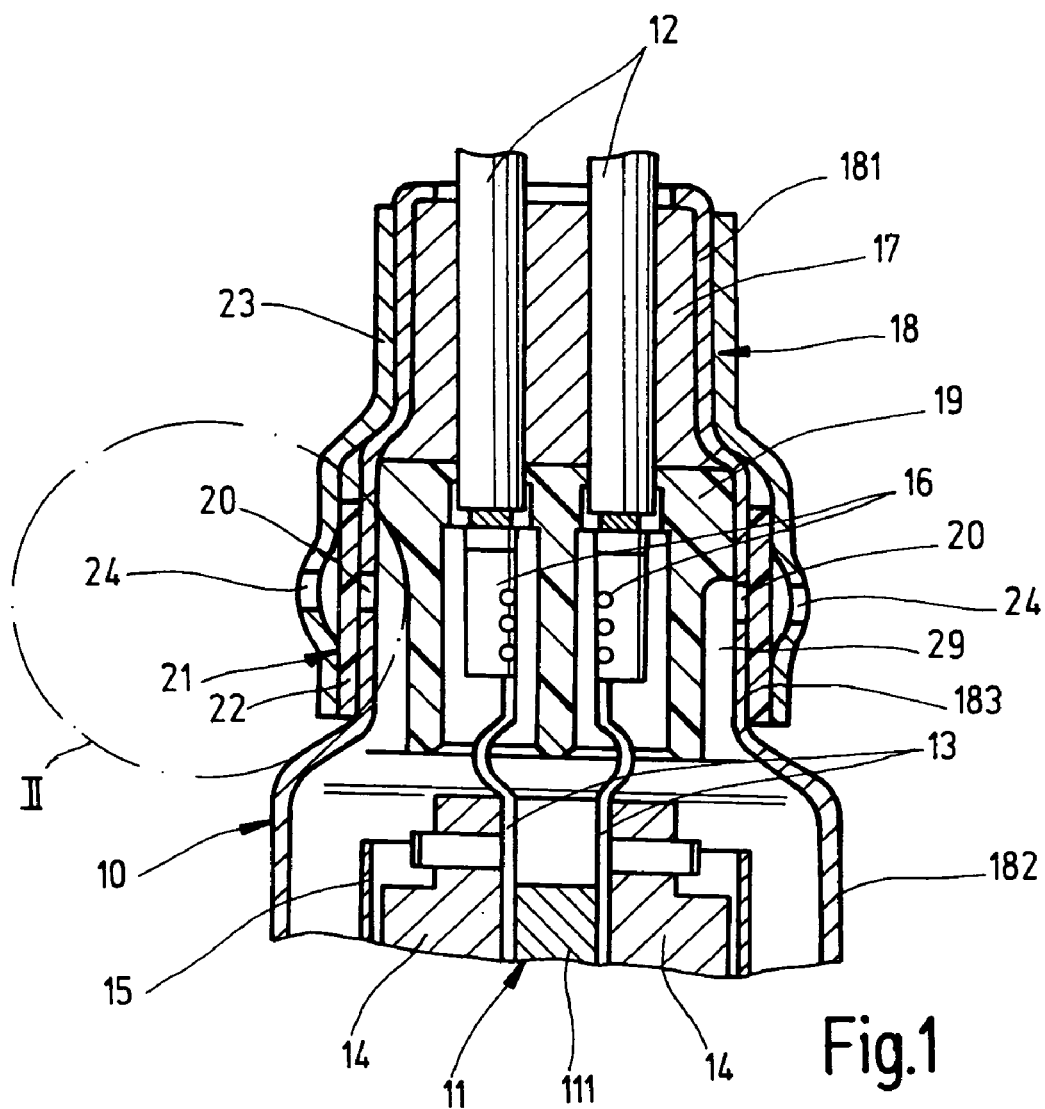
FIG. 1 shows a detail of a longitudinal section of a gas sensor for internal combustion engines.

The gas sensor for determining the concentration of a gas component of a measuring gas as an exemplary embodiment of a general detecting element, illustrated in FIG. 1 as a detail of a longitudinal section, is, for example, a lambda probe used to determine the oxygen content in the exhaust gas of an internal combustion engine. The gas sensor has a sensor element 11 which is accommodated in a detecting element housing 10 and has a measuring gas end section which is exposed to the measuring gas and a connecting end section 111 on which sensor element 11 is electrically contacted. Only connecting end section 111 of sensor element 11, having the connecting end of detecting element housing 10, and the contacting area of sensor element 11 located therein, is visible in FIG. 1. A complete representation of sensor element 11 is shown, for example, in DE 101 51 291 A1.

Connecting end section 111 of sensor element 11 has contact surfaces, which are not illustrated here, as well as an opening which communicates with a reference gas channel extending all the way to the measuring gas end section of sensor element 11. The contact surfaces of sensor element 11 are electrically connected to contact parts 13, which are pressed against the contact surfaces of sensor element 11 by a spring element 15 which engages with a connecting element 14. Contact parts 13 have crimp joints 16 which establish an electrical contact between contact parts 13 and connecting cables 12. Connecting cables 12 are routed from detecting element housing 10 through gas-tight cable bushing 127.

Cable bushing 17, contact parts 13 having crimp joints 16 and connecting end section 111 of sensor element 11 are surrounded by a protective sleeve 18 which is permanently connected to a metal housing member. The housing member, which is not illustrated here, usually includes a tapped hole and a hex nut for mounting the lambda probe onto the exhaust pipe of the internal combustion engine. Directly adjacent to cable bushing 17, protective sleeve 18 accommodates a supporting element 19 made of a solid PTFE material, which has a pot-shaped design and accommodates crimp joint 16 in its interior, providing a radial clearance from the cylindrical pot wall. The outer diameter of pot-shaped supporting element 19 is reduced in a section of the pot wall which continues toward the opening of the pot. This tapered section of supporting element 19 produces a ring-shaped flow path 29 between supporting element 19 and the inner wall of protective sleeve 18. Protective sleeve 18 is provided with multiple radially introduced holes, referred to here as radial openings 20, in the area of flow path 29. Protective sleeve 18 has a central sleeve section 183, an adjacent, collar-like, reduced-diameter sleeve section 181 and a larger-diameter sleeve section 182 that continues at the other end of central sleeve section 183. Collar-shaped sleeve section 181 surrounds cable bushing 17 and is flanged at one end onto the end face of cable bushing 17. Central sleeve section 183 overlaps supporting element 19, and sleeve section 182 having the largest diameter surrounds connecting end section 111 of sensor element 11 all the way to the housing member.

A flexible plastic hose 22, which acts as a gas-permeable diaphragm 21 and is preferably made of a gas-permeable PTFE material, is provided over central sleeve section 183 in such a way that radial openings 20 located in central sleeve section 183 are covered. A clamping sleeve 23, which extends over collar-type sleeve section 181 and permanently surrounds it, is mounted on plastic hose 22. In the overlap area with diaphragm 21, clamping sleeve 23 has multiple radial openings 24, which are located at the axial height of radial openings 20 in protective sleeve 18 and are preferably aligned with these radial openings 20 in such a way that a reference gas surrounding protective sleeve 18, e.g., atmospheric air, is able to pass through radial openings 24 in clamping sleeve 23, diaphragm 21, radial openings 20 and flow path 29 on supporting element 19 and enter connecting end section 111 of sensor element 11, from where it may pass to the reference gas channel of sensor element 11.

Figure 2:
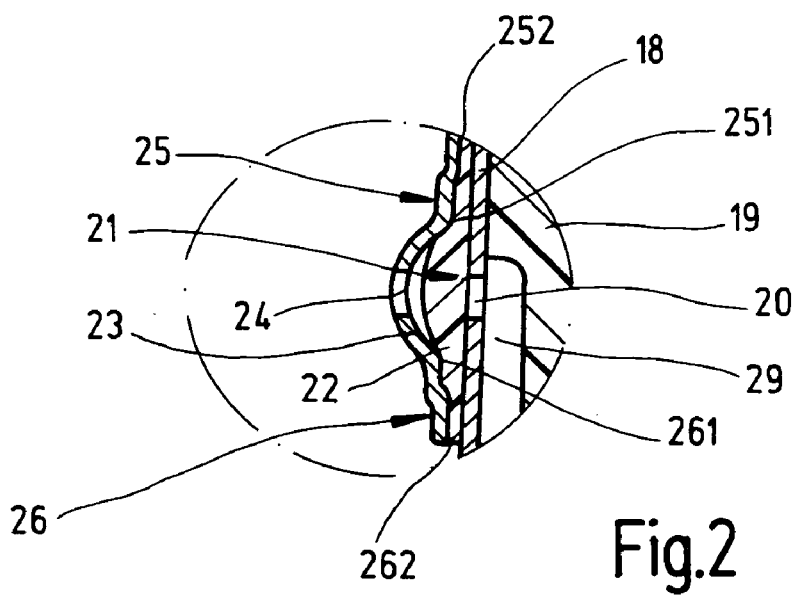
FIG. 2 shows section II illustrated in FIG. 1 following caulking of the clamping sleeve.

In the overlap area with diaphragm 21, clamping sleeve 23 is caulked axially above and below radial openings 20, 24 in protective sleeve 18 and clamping sleeve 23, as illustrated in an enlarged view in FIGS. 2 and 3. FIG. 1 shows an uncaulked view of clamping sleeve 23. Elastically deformable diaphragm 21 is compressed in the area of caulking zones 25, 26, i.e., the wall thickness of plastic hose 22 is reduced to fix plastic hose 22 in place and seal the hose ends against liquids penetrating in the axial direction between protective sleeve 18 and hose 22, which would cause the gas sensor to malfunction. To ensure that damage to diaphragm 21 due to poor manufacturing conditions during caulking and/or due to high thermal stress during operation does not result in leakage paths in the caulking area, both caulking zones 25, 26 running at an axial distance from each other are designed in such a way that the compression of diaphragm 21 increases from inner caulking edges 251, 261 facing each other to external caulking edges 252, 262 facing away from each other. The increase in compression of diaphragm 21 in the area of caulking zones 25, 26 may be either continuous or stepped.

Compression of diaphragm 21 to different degrees is achieved in that the radial clearance between deformation areas created in clamping sleeve 23 by caulking and protective sleeve 18 decreases along caulking zones 25, 26, starting from inner deformation or caulking edges 251, 261 facing each other and extending to outer deformation or caulking edges 252, 262 facing away from each other, and that the decrease in radial clearance is continuous or stepped.

Figure 3:
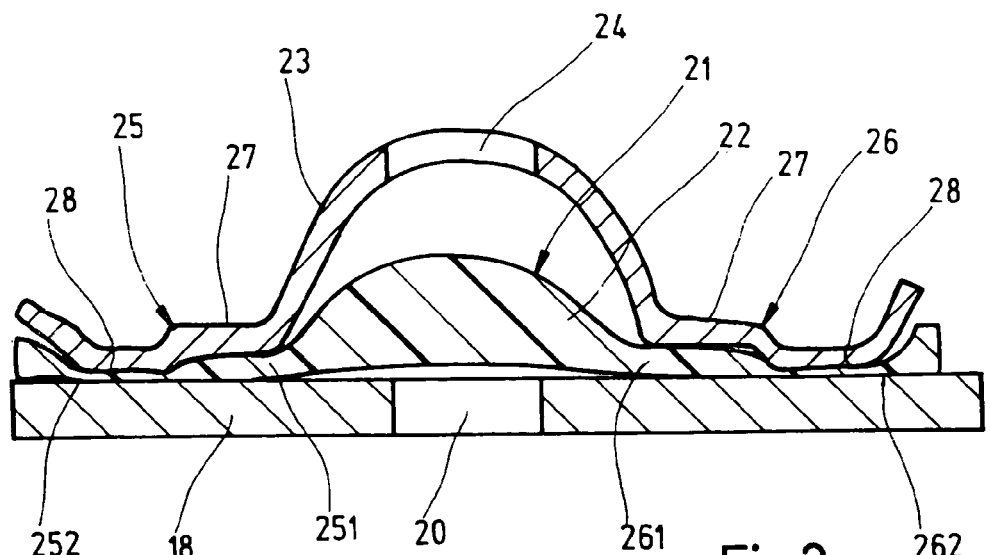
FIG. 3 shows an enlarged representation of the section in FIG. 2.

According to the exemplary embodiment illustrated in an enlarged view in FIG. 3, two deformation zones 27, 28, of which outer deformation zones 28 have a smaller radial distance from protective sleeve 18 than inner deformation zones 27, are provided in each of the deformation areas in clamping sleeve 23 along caulking zones 25 and 26, respectively. Consequently, the wall thickness of plastic hose 22 is much reduced to a greater extent in outer deformation zones 28 than it is in inner deformation zones 27 and amounts to approximately 10–20% of the wall thickness of non-deformed plastic hose 22 in outer deformation zones 28 and approximately 30–40% of the wall thickness of non-deformed plastic hose 22 in inner deformation zones 27.

Caulking zones 25, 26 are produced by a caulking punch 30 (FIGS. 4 through 6), which includes two axially spaced, bow-shaped caulking surfaces 31, 32 having two inner surface edges 311 and 321 which face each other in the axial direction and two outer surface edges 312 and 322 which face away from each other in the axial direction. Inner surface edges 311, 321 are recessed radially relative to external surface edges 312, 322, and the gradient between inner surface edge 311 and 321 and outer surface edge 312 and 322 in each caulking surface 31 and 32, respectively, is continuous or stepped.

Figure 5:
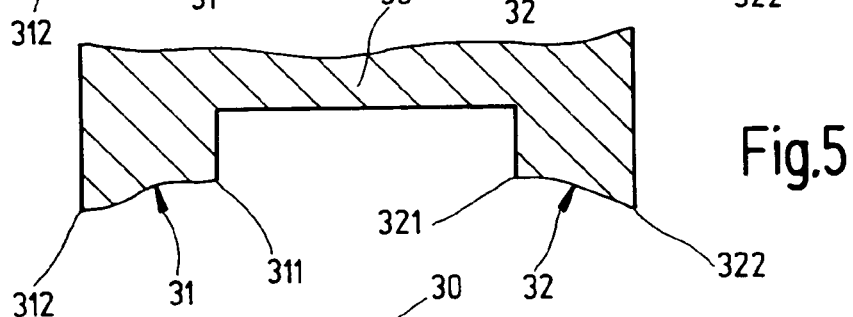
FIG. 5 is a second illustration showing a detail of an axial profile of a caulking punch according to a second exemplary embodiment.

According to the exemplary embodiment in FIG. 5, the gradient between external surface edges 311, 312 and 321, 322 of caulking surfaces 31, 32 is continuous. If a caulking punch 30 of this type, having a radial force of pressure, is applied to clamping sleeve 23, the latter is caulked onto protective sleeve 18, diaphragm 21 being compressed at a steady rate in each of resulting caulking zones 25, 26 to a continuously increasing degree from inner caulking edges 251 and 261 to outer caulking edges 252 and 262, respectively.

Figure 4:
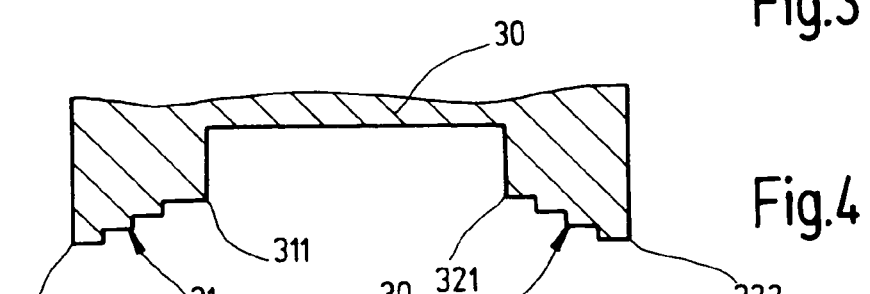
FIG. 4 is a first illustration showing a detail of an axial profile of a caulking punch according to a first exemplary embodiment.

The axial profile of caulking punch 30 illustrated in FIG. 4 achieves a stepped compression of diaphragm 21 during caulking. As shown in FIG. 4, the gradient of caulking surfaces 31, 32 from outer surface edges 312, 322 to inner surface edges 311, 321 is stepped. According to the exemplary embodiment in FIG. 4, each caulking surface has four surface steps so that, when this deformation punch 30 is applied, four deformation zones are produced in each caulking zone 25, 26 in clamping sleeve 23, the radial distance of these deformation zones from protective sleeve 18 increasing discretely from the outside to the inside.

Figure 6:
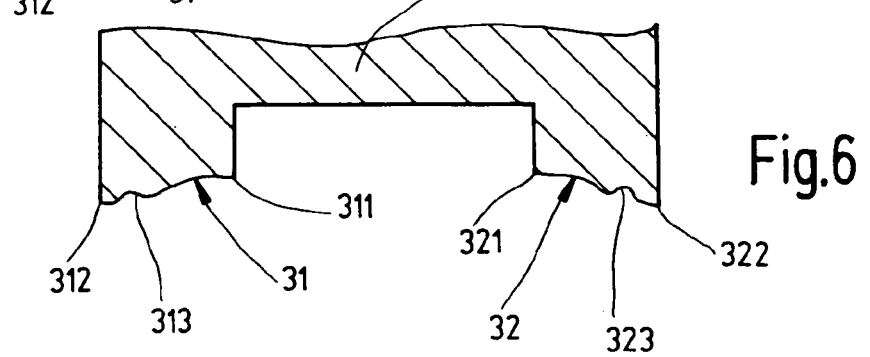
FIG. 6 is a third illustration showing a detail of an axial profile of a caulking punch according to a third exemplary embodiment.

The axial profile of caulking punch 30 illustrated in FIG. 6 is identical to the one in FIG. 5 except for the fact that an undercut 313 is formed in each caulking surface 31, 32 in the continuous surface gradient.

The present invention is not limited to the lambda probe described by way of example. It may also be used for other detecting elements, e.g., gas sensors for determining the nitrogen oxide content in the exhaust gas of internal combustion engines.

What is claimed is:

1. A detecting element, comprising:
    at least one connecting cable;
    a sensor element that is exposable to a measuring gas and includes a connecting end section, the connecting end section being contacted by the at least one connecting cable and being exposed to a reference atmosphere;
    a protective sleeve including at least one first radial opening provided on the connecting end section;
    a gas-permeable diaphragm that is slid on over the protective sleeve and covers the at least one first radial opening; and
    a clamping sleeve that overlaps the diaphragm and is provided with at least one second radial opening, wherein:
        the clamping sleeve is respectively caulked in a first caulking-around zone and a second caulking-around zone around axially above and below the at least one first radial opening and the at least one second radial opening in the protective sleeve and the clamping sleeve in an area of the clamping sleeve covering the diaphragm,
        the first caulking-around zone and the second caulking-around zone are designed in such a way that the diaphragm is compressed to an increasing degree from inner caulking edges facing each other to outer caulking edges facing away from each other
        a radial clearance between the clamping sleeve and the protective sleeve decreases in deformation areas in the clamping sleeve produced by the first caulking-round zone and the second caulking-around zone from the inner caulking edges facing each other to the outer caulking edges facing away from each other,
        the radial clearance decreases continuously, and
        a discontinuity forming an undercut is present in the continuous decrease in the radial clearance.

2. A detecting element, comprising:
    at least one connecting cable;
    a sensor element that is exposable to a measuring gas and includes a connecting end section, the connecting end section being contacted by the at least one connecting cable and being exposed to a reference atmosphere;
    a protective sleeve including at least one first radial opening provided on the connecting end section;
    a gas-permeable diaphragm that is slid on over the protective sleeve and covers the at least one first radial opening; and
    a clamping sleeve that overlaps the diaphragm and is provided with at least one second radial opening, wherein:
        the clamping sleeve is respectively caulked in a first caulking-around zone and a second caulking-around zone around axially above and below the at least one first radial opening and the at least one second radial opening in the protective sleeve and the clamping sleeve in an area of the clamping sleeve covering the diaphragm,
        the first caulking-around zone and the second caulking-around zone are designed in such a way that the diaphragm is compressed to an increasing degree from inner caulking edges facing each other to outer caulking edges facing away from each other,
        a radial clearance between the clamping sleeve and the protective sleeve decreases in deformation areas in the clamping sleeve produced by the first caulking-round zone and the second caulking-around zone from the inner caulking edges facing each other to the outer caulking edges facing away from each other,
        the radial clearance decreases in a stepped manner, and
        the deformation areas of a first deformation zone and a second deformation zone that are consecutive have a substantially constant radial clearance that decreases from the first deformation zone to the second deformation zone and is the smallest in those deformation areas of the second deformation zone which have the greatest axial distance from each other.

3. A detecting element, comprising:
    at least one connecting cable;
    a sensor element that is exposable to a measuring gas and includes a connecting end section, the connecting end section being contacted by the at least one connecting cable and being exposed to a reference atmosphere;
    a protective sleeve including at least one first radial opening provided on the connecting end section;
    a gas-permeable diaphragm that is slid on over the protective sleeve and covers the at least one first radial opening; and
    a clamping sleeve that overlaps the diaphragm and is provided with at least one second radial opening, wherein:
        the clamping sleeve is respectively caulked in a first caulking-around zone and a second caulking-around zone around axially above and below the at least one first radial opening and the at least one second radial opening in the protective sleeve and the clamping sleeve in an area of the clamping sleeve covering the diaphragm,
        the first caulking-around zone and the second caulking-around zone are designed in such a way that the diaphragm is compressed to an increasing degree from inner caulking edges facing each other to outer caulking edges facing away from each other,
        a radial clearance between the clamping sleeve and the protective sleeve decreases in deformation areas in the clamping sleeve produced by the first caulking-round zone and the second caulking-around zone from the inner caulking edges facing each other to the outer caulking edges facing away from each other, each deformation area has a first deformation zone having a greater radial distance from the protective sleeve and a second deformation zone having a comparatively smaller radial distance from the protective sleeve, and those deformation areas of the first deformation zone having a greater radial distance have the smaller radial distance from each other.

4. A method for manufacturing a detecting sensor, comprising:

providing a caulking punch with two axially spaced, bow-shaped caulking surfaces;

forming the caulking surfaces in an axial direction in such a way that inner surface edges facing each other are radially recessed relative to outer surface edges facing away from each other;

applying the caulking punch with a radial pressure to a clamping sleeve in such a way that the caulking surfaces are positioned axially above and below radial holes formed in a protective sleeve and the clamping sleeve, wherein a gradient of the caulking surfaces runs continuously from the outer surface edges to the inner surface edges; and forming an undercut in the continuous gradient of the caulking surfaces.

5. A method for manufacturing a detecting sensor, comprising:

providing a caulking punch with two axially spaced, bow-shaped caulking surfaces;

forming the caulking surfaces in an axial direction in such a way that inner surface edges facing each other are radially recessed relative to outer surface edges facing away from each other; and applying the caulking punch with a radial pressure to a clamping sleeve in such a way that the caulking surfaces are positioned axially above and below radial holes formed in a protective sleeve and the clamping sleeve; wherein gradient of the caulking surfaces is stepped from the outer surface edges to the inner surface edges and has at least two planar, radially offset surface sections.

* * * * *